(12) United States Patent
Kutushov

(10) Patent No.: US 8,436,195 B2
(45) Date of Patent: May 7, 2013

(54) USE OF MALACHITE GREEN OXALATE FOR TREATING MALIGNANT NEOPLASMS

(75) Inventor: Mikhail Vladimirovich Kutushov, Moscow (RU)

(73) Assignees: Evgeny Pavlovich Germanov, Moscow (RU); Mikhail Vladimirovich Kutushov, Moscow (RU)

( * ) Notice: Subject to any disclaimer, the term of this patent is extended or adjusted under 35 U.S.C. 154(b) by 0 days.

(21) Appl. No.: 12/312,898

(22) PCT Filed: Nov. 29, 2006

(86) PCT No.: PCT/RU2006/000639
§ 371 (c)(1),
(2), (4) Date: Dec. 21, 2009

(87) PCT Pub. No.: WO2008/066402
PCT Pub. Date: Jun. 5, 2008

(65) Prior Publication Data
US 2010/0105776 A1 Apr. 29, 2010

(51) Int. Cl.
*C09B 11/10* (2006.01)
*A61K 31/136* (2006.01)

(52) U.S. Cl.
USPC ........... 552/113; 552/101; 562/590; 514/648; 514/646; 514/579; 514/574

(58) Field of Classification Search .......... None
See application file for complete search history.

(56) References Cited

U.S. PATENT DOCUMENTS

| | | | | |
|---|---|---|---|---|
| 1,499,348 | A * | 7/1924 | Crane et al. | 514/784 |
| 2,532,206 | A * | 11/1950 | Taub et al. | 514/789 |
| 6,331,564 | B1 * | 12/2001 | Brugnara et al. | 514/520 |
| 2003/0114403 | A1 * | 6/2003 | Mihail et al. | 514/44 |

FOREIGN PATENT DOCUMENTS

GB 2 084 604 A 9/1950

OTHER PUBLICATIONS

"Antineoplastic Action of Malachite Green, An Experimental Study" by Ioachim, Cancer Chemo. Rep. 31, 41-46 (1963).*
"Toxicological studies on malachite green: A triphenylmethane dye" by Chemmensen et al., Arch. Toxicol. 56, 43-45 (1984).*
"Effects of Food on Clinical Pharmacokinetics" by Singh, Clin. Pharmacokinet. 37, 213-55 (1999).*
Ioachim H., "Antineoplastic action of malachite green—an experimental study," Cancer Chemotherapy Reports, Sep. 1963, No. 31, pp. 41-46.
Mashkovskii M.D., "Lekarstvennye sredsiva, posobie dlya vrachei," M. OOO "Novaya Bolna", Izd. S.V.Divov, 2001, t, 1, pp. 8-10.
Clemmensen S. et al., "Toxicological studies on malachite green: a triphenylmethane dye," Arch. Toxicol. Nov. 1984, 56(1):43-5 (Abstract).
Kutushov M.V. DCT, www.kutshov.com Jul. 25, 2007 "(anizotropiruyuschaya) terapiya, novoe napravlenie v onkologii," May 3, 2006 (9 pages).
http://women,city-portal.ru/2004/12/24, "Lechenie akvariumnykh ryb rastvorami malkhitovogo zelenogo," Dec. 24, 2004 (2 pages).

* cited by examiner

*Primary Examiner* — Brandon Fetterolf
*Assistant Examiner* — Theodore R West
(74) *Attorney, Agent, or Firm* — Pauley Petersen & Erickson

(57) ABSTRACT

The use of malachite green in the form of a tetramethyl-diamino-triphenyl-carbinol anhydro-oxalate $[(C_{23}H_{25}N_2)-(C_2HO_4)]_2-C_2H_2O_4$ of the following structural formula as a drug for treating malignant neoplasms administered in a single dose of 1 to 2 g. Malachite green can be used when dissolved in an aqueous solution or in a physiological salt solution or in spirit. In different cases, the malachite green solution is perorally administered before and after a meal or is injected per rectum, or a 1% malachite green solution is intravenously introduced, or the malachite green is applied as a rectal suppository component or as a component of 1-5% ointment. The medicinal agent exhibits an extended range of therapeutic actions with respect to different oncological diseases, is freely available, not expensive, non-toxic, does not generate side effects when used in pharmaceutically acceptable doses, and makes it possible to reduce a treating time and to increase the efficiency of treatment.

11 Claims, No Drawings

USE OF MALACHITE GREEN OXALATE FOR TREATING MALIGNANT NEOPLASMS

BACKGROUND OF THE INVENTION

1. Field of the Invention

This invention relates to medicine, namely to pluripotential medicinal preparations used for treatment of oncological diseases, and is labeled OF3.

2. Discussion of Related Art

There is a known medicinal preparation fluororacil, which is a white or slightly yellowish crystalline powder poorly soluble in water and alcohol. It is an antimetabolite. Its antitumor activity is determined by its transformation in cancerous cells into a competitive inhibitor that takes part in the synthesis of enzyme nucleic acids. For example, see M. D. Mashkovskiy, "Medications", Moscow, OOO Novaya volna, S. B. Divov publisher, 2002, v. 2, p. 425.

The preparation is administered intravenously in cases of inoperable and recurrent gastric carcinoma, rectal and colon cancer, breast cancer, ovarian cancer, and pancreatic cancer. However, the preparation is highly toxic, and when used, it can cause hematosis depression, diarrhea, anorexia, vomiting, and ulcerous stomatitis. In addition, the preparaton is counterindicated in cases of a patient's general grave condition, stomach and duodenal ulcer, and apparent liver insufficiency.

The closest analogue-prototype is the preparation "Rheaferon", a recombinant $\alpha_2$-interferon produced by a pseudomonade bacterial strain with human $\alpha_2$-interferon, manufactured in the form of porous powder, built into its genetic apparatus. Water solution of the preparation is prescribed for intramuscular or subcutaneous administration. For example, see M. D. Mashkovskiy, "Medications", Moscow, OOO Novaya volna, S. B. Divov publisher, 2002, v. 2, p.p. 323-324.

The preparation has antiviral, immunomodulating and antitumor activity. It is effective in the treatment of viral hepatitis and is used in treatment of hairy-cell leukosis, Kaposi's sarcoma, against an AIDS background, kidney cancer, metastatic melanoma, and the like. However, when using rheaferon, shakes, general indisposition, allergic skin reactions, and leuco- and trombocytpenia are possible. The preparation is counterindicated for allergic diseases, apparent liver and kidney diseases, and pregnancy.

SUMMARY OF THE INVENTION

One object of this invention is to provide a medication with a wide spectrum of therapeutic intervention with respect to various oncological diseases.

The technical result that ensures a solution of the problem is the use, as medication for treatment of oncological diseases, a widely available and inexpensive substance that is non-toxic, that does not cause side effects when used in pharmaceutically acceptable doses, and that reduces duration of treatment and increases treatment efficacy.

This invention uses malachite green in the form of ANHYDROOXALATE TETRAMETHYLDIAMISHTRIPHENOLCARBINOL $[(C_{23}H_{25}N_2)-(C_2HO_4)]_2-C_2H_2O_4$ that has the following structural formula:

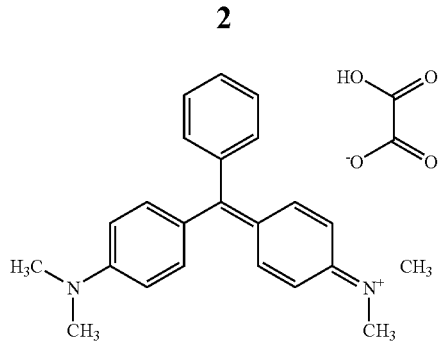

as medication for treatment of malignant neoplasms in doses from 1 mg to 2 g at a time. Malachite green can be used in the form of water solution, saline or alcohol solution. In various applications, the malachite green solution is administered perorally before or after meal, or the malachite green solution is administered rectally, or a 1% malachite green solution is administered intravenously, or the malachite green is administered rectally in suppositories, or the malachite green is administered in 1-5% ointment.

The chemical name of vegetable dye malachite green (Malachite Green oxalate salt), or ANHYDROOXALATE TETRAMETHYLDIAMISHTRIPHENOLCARBINOL, is (dimethylammo)benzhydrylidene]cyclohexa-2,5-dien-1-ylidene]dimethylammonium]oxalate, dioxalate; $N,N_5N',N'$-Tetramethyl-4,4[1]-diaminotriphenylcarbenium oxalate; CI. 42000; Malachite green oxalate; Victoria Green B). Manufacturer: Reagena, Finland. Synonyms: bensoilgreen, malachitegreen—a synthetic diamintriphenylmethane dye. The green or yellow crystals with metallic luster are very soluble in water, alcohol and saline.

Currently the malachite green is used in microscopy for intravital staining of cell nuclei, for staining of erythrocites and ascaride eggs, and as medicine in treatment of aquarium fish infection diseases. The premise of dyes action on the structure of malignant cells is as follows. In oncological (cancer) cells, polarization and anisotropy are disturbed, and as a result so is the spontaneous cell glow. Photoactivity of structures plays a key role in vital activity of cells. Many biochemical reactions and cell mitosis are accompanied by photochemical reactions and this can be characterized as quantum mechanical phenomena. By acting on these mechanisms, it is possible to treat not just cancer, but a lot of other diseases (see the book "Cancer Is Curable", M. V. Kutushov, V. Sekachev publisher, Moscow, 2005, p. 393). In cancer, partial disturbances of cell structures, and first of all abnormal stacking of proteins, occur. It is known from physics that the value of ultimate polarization is related to molecule symmetry. In the case of cancerous degeneration of cell structures, oscillators' linkage with the molecule looses its stiffness. Thus, the degree of molecule anisotropy and also the degree of polarization decrease. This determines that even in case of completely anisotropic molecules the degree of polarization does not reach its ultimate theoretical value. Thus, if we introduce an acceptable dye into such system, they must be "equalizing" the degree of polarization and restoring the disturbed dissymmetry and anisotropy. Organic dyes have somewhat the property of generating radiation. In generation spectra of most dyes, a number of sharp equidistant lines are observed and the distance between the lines depends on properties of the resonator. The resonator has a lot of reflecting surfaces. If a cell itself and its structures are used as resonators, the resonant properties would change depending on the norm and pathology. In the case of cancer, cell and tissue structures are disturbed in the most violent way.

All dye molecules have a flat skeleton. Very seldom groups of radicals leave the common plane. Malachite green, like triphenylmethane dyes and a number of other dyes, does not fluoresce in solutions because their structure allows rotation of radical groups about chains of conjugated links. In solid solutions (liquid crystals) they glow brightly. Cancer proteins are located in rigid cubic syngonies. Thus, such dyes glow in them, and play the role of quantum oscillators. At the same time, the dyes have high absorptivity in a visible spectrum. Thus, when interacting with such structures the dyes give them back their original narrow absorption spectra, or in other words so-called equidistant properties.

Thus, one can conclude that, by themselves or jointly with cell structures, they can cancel out the wavelength "used" by cancerous structures for their vital activity thus causing their death. These properties of dyes are instrumental in cancer therapy. It is well known that in symmetric and asymmetric dyes with the order of symmetry higher than two, the ultimate polarization practically does not change when the wavelength of excited light changes within the long-wave absorption band. In triphenylmethane dyes, the degree of polarization changes sharply when the wavelength of excited light changes within this absorption band. Thus, a non-toxic dye, malachite green, which can generate and self-generate photons with required length, was chosen empirically. Malachite green changes its color from green to blue in a very narrow range even with an insignificant amount of photons (light). This property, as in no other dye, meets all requirements to dyes used in the treatment of cancer. This mechanism has been used as the basis for selective suppresion of cancerous structures.

Studies that were conducted have demonstrated that the medicine, malachite green, in the form of oxalate has antineoplastic action, including also with respect to leucoses, by objective manifestation of antineoplastic therapeutic effect. This was confirmed by instrumental laboratory examinations by conducting patients' blood tests and measuring tumor dimensions before and after administration of the respective preparation, malachite green.

It can be administered perorally, rectally or intravenously if it is dissolved, strained, filtered, recrystallized and sterilized.

The medicinal preparation based on malachite green can be administered perorally as powder or tablets with or after a meal, rectally in the form of suppositories, or externally in the form of suspensions or ointments. Its use in a wide range of doses (from 1 mg to 2 g) does not cause allergic reactions or other side effects, and its efficacy (in treatment of respective diseases) is not lower than for instance efficacy of the preparation selected as the prototype.

The results of studying the action mechanism of the proposed medicinal preparation are provided in examples No. 1-5, and the possibility of using it for treatment is supported by examples No. 6-15.

EXAMPLE NO. 1

In experimental group vials with cancer cells PC-3 (prostate carcinoma) in buffer solution (10 ml), a medicinal preparation diluted to $10^{-5}$ mmol/l was added in the form of malachite green solution.

In addition, adriamycin, rheaferon and saline, respectively, were added, with the same dilution, to vials with the same pool of cancer cells. A control group was also formed consisting of the same number of vials with the same components except cancer cells, and instead, fibroblasts were put in the group vials.

After thermostatting for 72 hours at 37° C. the contents of the above vials was analyzed.

Examination of the results has demonstrated the following.

In the experimental group vials with the medicinal preparation, mitochondria membranes were practically completely destroyed, and the pattern was much the same for all versions of the medicinal preparation used. In the group's vials with adriamycin, membrane swelling was observed. With rheaferon, membrane swelling with partial (about 60%) destruction was observed. No changes were detected in cells in the vial with saline.

In the control group vials, mitochondria membranes were swelled, but their integrity was preserved.

The data indicate that the proposed medicinal preparation causes destriction of mitochondria membranes of cancer cells but does not change the structure of normal cells. In other words, the medicinal preparation enhances cell mitochondrias ability to produce enzymes that cause apoptosis of cancer cells.

EXAMPLE NO. 2

To 4 vials of the experimental group with cancer cells MCF-7 (breast adenocarcinoma) in a buffer solution (10 ml), a medicinal preparation diluted to $10^{-5}$ mmol/l was added in the form of malachite green solution.

The control group, saline was added to one vial, and adriamycin and rheapheron were added to other vials with the same pool of cancer cells.

In vials of both groups, cytochrome-C titers were determined, and they were 1:14000.

After thermostatting for 24 hours at 37° C. the contents of the above vials was analyzed. Examination of the results has demonstrated the following.

In the control group vials with the medicinal preparation added, cytochrome-C titer for the vial with malachite green was 1:2000.

In vials with adriamycin and rheaferon, the titer was 1:12000 and 1:9600, respectively. In the vial with saline, no particular changes were detected.

The results suggest that the proposed medicinal preparation facilitates release of "aggressive" cytochrome-C protein from cancer cells mitochondria membranes. This triggers the DNA destruction mechanism, which causes apoptosis of cancer cells.

EXAMPLE NO. 3

To a vial (10 ml) with blood plasma transthyretin (protein) (pH-7.0), concentration 0.05 mmol/ml, 4 drops of 0.1% water solution of malachite green were added.

The vial was placed in a thermostat (incubator) at 37° C. After 15 minutes, the transthyretin concentration and plasma pH were measured.

No transthyretin was selected, pH-6.0.

It follows that this medicinal preparation affects protein denaturation not as an acid but as a preparation that changes polymer structure.

This feature determines the therapeutic effect of this medicinal preparation, for instance, when treating malignant tumors.

EXAMPLE NO. 4

Blood of a patient with sarcoma (10 ml) was centrifuged. Part of the resulting plasma was dried and photographed in a polarization microscope. Water solution of malachite green was added to the other part of the plasma, and the resulting mixture was photographed in a polarization microscope.

Results include that light scattering occurs in the first composition, and birefringence occurs in the second composition.

The data indicate that this medicinal preparation returns back to norm protein folding that was changed in cancer.

EXAMPLE NO. 5

Filtrate from melanoma-16 (10 ml) was placed in a quartz cuvet and photographed in a polarization microscope.

Then, malachite green solution was added to the filtrate, and it was again photographed in polarized light.

Results include that in pictures with no preparation, light polarization is negligible and in pictures after adding the preparation there is apparent polarization of the beam passing the composition.

The data indicate that this medicinal preparation causes structural changes in cancer cells proteins.

Examples of treatment follow.

EXAMPLE NO. 6

Patient V., 49 years old. Diagnosis: lung adenocarcinoma. Metastases to the brain. Cachexia. On CT, several tumor masses in the mediastinym and right lung, each 2.7×2.9×3.0 cm on average. A grave condition, dyspnea, cyanosis, adynamia, painful sensations exacerbated when coughing. Prescribed treatment included the use of antitumor medicinal preparation. The first course of treatment with the preparation—15 drops of a 1% solution in a glass of water 3 times a day perorally, also a microclyster at lunch—10 drops of a 1% solution in 30 ml of water, and overnight a 1% suppository with the preparation. For a week the condition had not changed essentially. However, the patient noted that for several hours after the sessions a substantial improvement of the pain syndrome was observed. By the third week after the treatment began, the patient's condition improved. Three months after the treatment with the preparation began no brain metastases were observed on CT. The lung tumor had shrunk to 1.3×1.21×2 cm. After six months of treatment the tumor had shrunk to 0.5×0.7×2.0 cm. No brain metastases were observed, dyspnea diminished, and the pain syndrome was practically absent. Against the treatment background, blood tests have normalized.

EXAMPLE NO. 7

Patient T., 33 years old.

Three years ago the right kidney was removed, and preventive chemotherapy was performed for renal cell carcinoma. During CT examination, a 2.5×4.4×3.2 cm tumor mass in the projection of the right kidney, as well as three round tumor masses 3.0 to 3.3 cm in diameter in the left lung.

A grave condition, dyspnea, cyanosis, adynamia.

Prescribed treatment included the use of an antitumor medicinal preparation. Preparation malachite green was administered perorally as a drink, 16 drops of a 1% solution three times a day, and in the form of microclysters. After 2 weeks of treatment dyspnea had diminished, and so had the pain syndrome. Against the treatment background, blood tests had normalized within 3 weeks. Then the course was repeated: for 6 months, the preparation was administered rectally in the form of 1% suppositories and by inhaling. During the therapy, the right kidney tumor and lung metastases disappeared. The weight was restored.

EXAMPLE NO. 8

Patient B., 62 years old. Diagnosis: bladder cancer. Metastases in pelvis bone. Three years ago, bladder resection had been performed for cancer. Complaints of pain, blood in urine and frequent urination. On CT, a 1×2×1 cm tumor mass in the orifice of projection of the right ureter. Two 1 to 2 cm in diameter tumor masses with uneven contours in the right wing of ilium.

A moderately grave condition, paleness of skin integument. Treatment with the preparation was started: 20 drops of a 1% solution of malachite green in half a glass of water perorally and in the form of microclysters. The course lasted 2 months. Over the course of treatment the tumor shrank to 0.2×0.2×0.2 cm. Metastates in the pelvis bone shrank by 1.5 cm. Biophosphonates were prescribed for replacement therapy. During the second week after treatment began, bleeding and the pain syndrome diminished. Against the treatment background, blood tests normalized within 4 weeks. The full course of treatment was administered for 6 months. Over the course of the therapy, the bladder tumor and pelvis metastases disappeared. The weight was restored.

EXAMPLE NO. 9

Patient V., 23 years old. Diagnosis: right-side brain glioblastoma.

Relapse. Two years ago tumor extirpation was performed for brain glioblastoma. Complaints of headaches, nausea, vomiting. A 2.2×2.4 cm tumor with uneven edges in brain substance is seen in NMRT in the projection of the postoperative scar. A moderately grave condition, paleness of skin integument. Preparation malachite green, 500 mg per 500 ml of sterile saline, intravenously by drop infusion was prescribed. The procedure lasted 60 minutes. Subsequent procedures were performed twice a week in exactly the same sequence. The course lasted 2 months. Over the course of treatment the tumor had shrunk to 0.1×0.2 cm. After two infusions of the preparation the nausea and pain syndrome diminished. Single dosing of the preparation had been administered every two weeks for six months. After 8 months of treatment no tumor was detected on CT.

EXAMPLE NO. 10

Patient L., 64 years old. Diagnosis: hepatoma. Primary liver cancer. 2 years ago resection of the right lobe of liver with a tumor for hepatoma was performed. Complaints of pain in the right hypochondrium, dyspnea, ascites, and periodic stool retention. A moderately grave condition, subnutrition, biliousness of skin integument. A 3×4 cm tumor with uneven edges in the left lobe of the liver is detected in the US. The umbilical vein bougienage was performed on the patient. Sterile preparation malachite green—100 mg diluted in 30 ml of saline—was administered via a catheter twice a day for 2 weeks. Subsequent procedures were performed in exactly the same sequence 3 times a week, but the preparation was administered intravenously. The course lasted 2 months. Over the course of treatment the tumor in the area had shrunk to 0.3×0.2 cm. After four months, in the place of tumor in the liver there was probably just a 0.1×0.1 cm fibroscar. During the process of treatment with the preparation, positive dynamics was being detected in blood tests.

General Blood Test Results

| Main Indexes | Dec. 10, 2003 | Dec. 29, 2003 | Feb. 04, 2004 | Apr. 07, 2004 |
|---|---|---|---|---|
| Erythrocytes | 3.22 | 3.60 | 4.37 | 4.67 |
| Hemoglobin | 74 | 80 | 117 | 123 |
| Thrombocytes | 315 | 362 | 286 | 310 |
| Leucocytes | 7.2 | 7.8 | 5.8 | 6.7 |
| Basophils 0-1% | 1 | — | — | 1 |
| Eosinophils 0-5 | 1 | 2 | 2 | 1 |
| Nuclear bacilli 1-6% | 1 | 1 | — | — |
| Nuclear segments 45-70 | 2 | 4 | 6 | 5 |
| Shift indexes | 39 | 43 | 56 | 67 |
| Lymphosytes 18-40% | 9 | 13 | 28 | 17 |
| Monocytes 2-9% | 15 | 16 | 37 | 39 |
| ESR 1-15 mm/h | 3.5 | 4.5 | 5.0 | 8.5 |

Biochemical Blood Test Results

| Main Indexes | Norm | Dec. 10, 2003 | Dec. 20, 2003 | Feb. 04, 2004 | Apr. 07, 2004 |
|---|---|---|---|---|---|
| Total protein | 65.0-85.0 gl [expansion not given; possibly g/l] | 44.43 98.0 | 45.90 83 | 68 79 | 65.64 67 |
| Creatinine | 44-110 | 7.2 | 6.4 | 4.1 | 2.6 |
| Urea | 1.66-8.3 | 6.21 | 5.62 | 5.75 | 7.03 |
| Cholesterol | 2.90-6.54 | 11.0 | 24.2 | 8.4 | 8.0 |
| Bilirubin | 8.5-20.5 | 3.0 | 22.3 | 3.3 | 2.0 |
| Total | Up to 25% | 8.0 | 11.9 | 5.1 | 6.0 |
| Bilirubin | Up to 25% | 82 | 96 | 84 | 90 |
| Conjugated | Up to 100 El | 107.2 | 102 | 89 | 78.0 |
| Bilirubin | 95-100.0 | 114.0 | 140 | 102.8 | 110.0 |
| Unconjugated | 135.0-147.0 | 114.20 | 115.3 | 114.31 | 134.2 |
| Amylase | | 3.8 | 4.9 | 4.8 | 4.9 |
| Chlorine | 3.5-6.0 | 2.72 | 2.32 | 2.28 | 2.15 |
| Sodium | 0.98-1.30 | 19.4 | 13.4 | 18.0 | 17.7 |
| Potassium | 2.1-2.55 | 314.3 | 395.8 | 138.0 | 64.4 |
| Calcium | zh [expansion not given] 8.8-27.0 | 190.4 | 224.7 | 94.4 | 43.7 |
| Ionized Calcium | 5-40 El | 564.4 | 431.7 | 113.8 | 30.4 |
| Total | 5-40 El | 765.8 | 526 | 254.2 | 48 |
| Iron serum | zh up to 104 | 5.71 | 5.48 | 4.55 | 6.7 |
| AST | El | 876 | 456 | 432 | 342 |
| GPT | 225-450 | | | | |
| Phosphatase alkaline | El | | | | |
| LDH | | | | | |

Currently, no complaints.

EXAMPLE 11

Patient T., 58 years old. Diagnosis: non-Hodgkin's lymphoma. Cachexia. One and a half years ago, a complete polychemotherapy course was administered. Six months ago tumor masses appeared on the neck and under the jaw. In the X-ray picture, mediastinum dilation was detected. At admission, complaints of dyspnea, weakness and hyperhydrosis.

A moderately grave condition, subnutrition, pale skin integument. A 2×3 cm tumor mass on the left side of the submaxillary area. On the neck, 2×3.3×4 cm tumor masses on both sides. Treatment with preparation malachite green was administered according to the following regimen: 20 drops of a 1% solution of malachite green diluted in 150 ml of water taken perorally three times a day. The course lasted 4 months. Twelve days after the treatment began, the submaxillary lymphnodes had disappeared completely. Over a month, tumors in the neck area shrank to 0.3×0.4 cm. Three months later, no lymphnodes were detected. The blood test and urinalysis are normal. The weight has been restored. No complaints.

EXAMPLE 12

Patient B., 45 years old. Diagnosis: large intestine adenocarcinoma. Metastases in liver.

Ascites. Three and a half years ago, large intestine resection was performed, and end-to-end anastomosis was applied. The patient underwent a complete polychemotherapy course.

Two years after treatment, abdominal cramps and tenesmus appeared. At admission, the patient complained of acute weakness, continuous abdominal pain, cough, dyspnea, ascitis and stool retention. A grave condition, subnutrition, pale skin integument with cyanotic tinge, the abdomen with signs of ascites. In blood tests, reduction of the number or erythrocites, hemoglobin, leukocites and albumin was observed, as well as increase of GPT and AST. In computer tomography, a 2×4 cm irregular shape mass with uneven edges was detected in the liver right lobe. In the anastomosis area, a 4×5.4 cm mass lesion and free fluid in the abdominal cavity were detected. Preparation malachite green was prescribed in the form of intravenous infusions, microclysters and drink. The infusion solution was 200 mg of sterilized malachite green diluted in 500 ml of saline. Infusions were administered weekly for 3 months. Microclysters were a mixture of 20 drops of a 1% solution of malachite green in 30 ml of boiled water. Microclysters were administered three times a day for 2 months. To enhance therapy, the preparation was taken in the form of a 1% solution of malachite green in 200 ml of boiled water 20 minutes before meal, three times a day. Ten days after the treatment began, the pain disappeared completely, and the patient gained appetite. During the third week of treatment, dyspnea diminished. During treatment, the tumor in the anastomosis area shrank to 0.2×0.3 cm. After 3 months there was a one-month break, and then the therapy was continued for 2 more months. Over the course of treatment, no metastases in liver or tumor in the anastomosis area were detected. Apparent stage improvement of blood indexes directly related to the therapy using the preparation was detected.

General Blood Test Results

| Main Indexes | Oct. 9, 2004 | Nov. 24, 2004 | Dec. 09, 2004 | Sep. 01, 2005 |
|---|---|---|---|---|
| Erythrocytes | 2.80 | 3.84 | 4.44 | 4.62 |
| Hemoglobin | 74 | 110 | 115 | 128 |
| Thrombocytes | 320 | 310 | 326 | 440 |
| Leucocytes | 9.2 | 12.0 | 5.2 | 5.3 |
| Basophils 0-1% | 1 | — | — | 1 |
| Eosinophils 0-5 | 1 | 2 | 2 | 1 |
| Nuclear bacilli 1-6% | 0 | 1 | — | 2 |
| Nuclear segments 45-70 | 2 | 6 | 6 | 5 |
| Lymphosytes 18-40% | | | | |
| Monocytes 2-9% | 1.0 | 24 | 32 | 39 |
| ESR 1-15 mm/h | 3.2 | 3.7 | 5.1 | 5.9 |

| Biochemical Blood Test Results | | | | | |
|---|---|---|---|---|---|
| Main Indexes | Norm | Oct. 9, 2004 | Nov. 24, 2004 | Dec. 09, 2004 | Sep. 01, 2005 |
| Total protein | 65.0-85.0 gl | 50.30 | 60.19 | 69 | 83.52 |
|  |  | 118.0 | 89 | 74 | 69 |
| Creatinine | 44-110 | 8.2 | 7.4 | 3.1 | 2.9 |
| Urea | 1.66-8.3 | 6.21 | 5.62 | 5.75 | 7.03 |
| Cholesterol | 2.90-6.54 | 11.0 | 24.2 | 8.4 | 8.0 |
| Bilirubin | 8.5-20.5 | 3.0 | 22.3 | 3.3 | 2.0 |
| Total | Up to 25% | 8.0 | 11.9 | 5.1 | 6.0 |
| Bilirubin | Up to 25% | 82 | 96 | 84 | 90 |
| Conjugated | Up to 100 El | 107.2 | 102 | 89 | 78.0 |
| Bilirubin | 95-100.0 | 114.0 | 140 | 102.8 | 110.0 |
| Unconjugated | 135.0-147.0 | 114.20 | 115.3 | 114.31 | 134.2 |
| Amylase |  | 3.8 | 4.9 | 4.8 | 4.9 |
| Chlorine | 3.5-6.0 | 2.72 | 2.32 | 2.28 | 2.15 |
| Sodium | 0.98-1.30 | 19.4 | 13.4 | 18.0 | 17.7 |
| Potassium | 2.1-2.55 | 314.3 | 395.8 | 138.0 | 64.4 |
| Calcium | zh 8.8-27.0 | 190.4 | 104.7 | 54.8 | 42.9 |
| Ionized | 5-40 El | 165.7 | 145.8 | 45.7 | 29.5 |
| Calcium | 5-40 El | 465.8 | 326 | 159.2 | 79 |
| Total | zh up to 104 |  |  |  |  |
| Iron serum | El | 523 | 432 | 342 | 228 |
| AST | 225-450 |  |  |  |  |
| GPT | El |  |  |  |  |
| Phosphatase alkaline |  |  |  |  |  |
| LDH |  |  |  |  |  |

The weight was restored. No complaints for 2 years.

EXAMPLE NO. 13

Patient K., 65 years old.

At admission, complaints of urethralgia and urine retention and redness. During examination: US on Feb. 4, 2001—prostate≈93 cm$^3$, a 32×42 mm tumor with fuzzy contours. PSA on Feb. 2, 2001—49.9 mg/ml. Needle biopsy—hyperplastic prostate.

Diagnosis: hyperplastic prostate. The patient declined surgery and chemotherapy.

Treatment with medicinal preparation malachite green was administered.

For 20 days beginning Mar. 9, 2001 the patient was taking powder preparation malachite green—300 mg with meal, and 30 minutes later 200 mg of malachite green, twice a day. Before going to bed, a suppository with 2% preparation was inserted. During this period pain during urination diminished, and urine color normalized. In ultrasound investigation, prostate volume shrank by 40%, the tumor got clear contours, its size was 13×14 mm$^2$. Then the therapy continued for two weeks: 300 mg of malachite green twice a day with meal; also daily therapeutic enemas before going to bed were prescribed—2.0 g of malachite green in 50 ml of boiled water.

During subsequent examination, according to the patient, complete disappearance of symptoms of the disease (urethralgia and on urine retention, etc.) was noted. In control US: prostate≈45 cm$^3$, the tumor shrank to 9×5 mm$^2$. PSA on May 9, 2001—1.1 mg/ml. No relapse has been noticed for 3 years.

EXAMPLE NO. 14

Patient T., 52 years old.

In 2001, because left ovarian carcinoma had been detected, hysterectomy and parovarium extirpation was performed. Chemotherapy courses for 2 years after the surgery.

At the end of July 2002, rectum pain and tenesmus appeared. In CT on Sep. 12, 2001, a 13.0×12.5 cm tumor between the rectum and bladder, which had extended through their walls, was detected.

Diagnosis: recurring left ovarian carcinoma. Because of ineffectiveness of continuing chemotherapy, treatment with the preparation in the form of microclysters was performed. At the beginning, 300 mg of malachite green daily was taken for 21 days.

On the 3$^{rd}$ day after the treatment began, the pain diminished, and urges to urinate and defecate became less frequent. In US: in 2 weeks the tumor was 4.2×3.0 cm$^2$, in another 4 weeks—1.4×1.2 cm$^2$; a clear boundary between the tumor and rectum and bladder walls was detected.

In control US 3 months later, a 0.4×0.5 cm$^2$ round mass with clear boundaries was detected.

During follow-up examination, the condition was satisfactory. In US on Mar. 21, 2005, a 0.4×0.3 cm$^2$ mass with clear contours was observed. Currently the patient is healthy.

EXAMPLE NO. 15

Patient T., 45 years old. Diagnosis: right kidney mesonephroma. Metastases in lungs.

The patient had undergone several chemotherapy and immunotherapy sessions. The tumor and metastases were continuing to grow. Malachite green treatment was proposed—50 mg diluted in 150 ml of water three times a day 20 minutes before meal. Overnight, 5% suppositories rectally. The treatment per this regimen continued for 3 months.

In CT 4 months later, the primary tumor was not detected, small-size metastases in the right lung, with signs of calcification.

EXAMPLE NO. 16

Patient Sh., 75 years old. Diagnosis: skin cancer. A 12×15×12 cm lesion focus in the right lower leg area. Hystologic diagnosis: skin cancer. Treatment with malachite green-based 2% ointment was performed. Over 2 months the tumor shrank 70%. Three months later, hyperpigmentation was detected in place of tumor. The patient has no complaints. There have been no relapses for 3 years.

Thus, a medicinal preparation with a wide range of therapeutic action with respect to various oncological diseases has been found. This provides the use, as a preparation for treatment of oncological diseases, of a widely available and inexpensive substance that is non-toxic, does not cause side effects when used in pharmaceutically acceptable doses, reduces the length of treatment, and increases treatment efficacy.

The invention claimed is:

1. A method, comprising administering to a human having malignant neoplasms, malachite green in a form of ANHYDROOXALATE TETRAMETHYLDIAMINOTRIPHENYLCARBINOL $[(C_{23}H_{25}N_2)—(C_2H_2O_4)]_2—C_2H_2O_4$ that has a following structural formula:

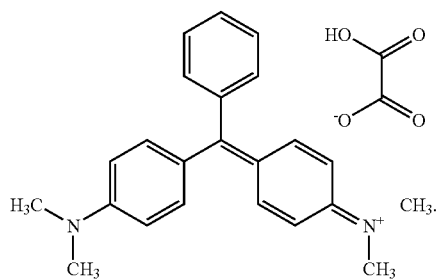

as preparation for treatment of malignant neoplasms.

2. The method according to claim 1, wherein the malachite green is used as a solution in water, or in saline, or in alcohol.

3. The method according to claim 2, wherein a water solution of the malachite green is taken with a meal.

4. The method according to claim 2, wherein the solution of malachite green is administered rectally.

5. The method according to claim 2, wherein a 1% by weight solution of the malachite green is administered intravenously.

6. The method according to claim 1, wherein the malachite green is used rectally in a suppository.

7. The method according to claim 1, wherein the malachite green is used in a 1-5% by weight ointment.

8. The method according to claim 1, wherein the malachite green is administered rectally in a solution.

9. The method according to claim 1, wherein a 1% by weight solution of the malachite green is administered intravenously.

10. The method according to claim 1, wherein the malignant neoplasms comprise sarcoma.

11. The method according to claim 1, wherein the malignant neoplasms comprise melanoma.

\* \* \* \* \*